United States Patent
Puri

(10) Patent No.: US 9,108,013 B2
(45) Date of Patent: Aug. 18, 2015

(54) AUTOMATIC ANAESTHESIA DELIVERY SYSTEM

(75) Inventor: Goverdhan Dutt Puri, Chandigarh (IN)

(73) Assignees: Post Graduate Institute of Medical Education and Research, Department of Anaesthesiology and Intensive Care, Chanlgarh (IN); The Secretary, Department of Information Technology, Ministry of Communication and Information Technology, New Delhi (IN)

(*) Notice: Subject to any disclaimer, the term of this patent is extended or adjusted under 35 U.S.C. 154(b) by 717 days.

(21) Appl. No.: 12/683,000

(22) PCT Filed: Oct. 15, 2008

(86) PCT No.: PCT/IN2008/000674
§ 371 (c)(1),
(2), (4) Date: May 5, 2010

(87) PCT Pub. No.: WO2009/050736
PCT Pub. Date: Apr. 23, 2009

(65) Prior Publication Data
US 2010/0241064 A1 Sep. 23, 2010

(30) Foreign Application Priority Data
Oct. 15, 2007 (IN) .......................... 2158/DEL/2007

(51) Int. Cl.
*A61M 16/01* (2006.01)
*A61M 5/145* (2006.01)
(Continued)

(52) U.S. Cl.
CPC ............ *A61M 16/01* (2013.01); *A61M 5/1452* (2013.01); *A61M 5/1723* (2013.01); *A61M 16/18* (2013.01);
(Continued)

(58) Field of Classification Search
CPC ... A61M 5/172; A61M 5/1723; A61M 16/00; A61M 16/01
USPC ............................... 604/66–67; 600/532, 544
See application file for complete search history.

(56) References Cited

U.S. PATENT DOCUMENTS 6,631,291 B2 * 10/2003 Viertio-Oja et al. .......... 600/544
6,745,764 B2 * 6/2004 Hickle ..................... 128/203.12
(Continued)

FOREIGN PATENT DOCUMENTS

EP 1547631 A1 * 6/2005
WO 0183007 A2 11/2001

OTHER PUBLICATIONS

Locher et al., "A New Closed-Loop Control System for Isoflurane Using Bispectral Index Outperforms Manual Control", American Society of Anesthesiologists, Inc., Sep. 2004, pp. 591-602, vol. 101, No. 3, Lippincott Williams & Wilkins, Inc.
Liu et al., "Titration of Propofol for Anesthetic Induction and Maintenance Guided by the Bispectral Index: Closed-loop verses Manual Control", American Society of Anesthesiologists, Inc., Apr. 2006, pp. 686-695, vol. 104, No. 4, Lippincott Williams & Wilkins, Inc.

Primary Examiner — Nicholas Lucchesi
Assistant Examiner — Melissa A Snyder
(74) Attorney, Agent, or Firm — The Webb Law Firm

(57) ABSTRACT

This invention relates to an improved automatic anaesthesia delivery system comprising: (a) at least one of a bispectral index monitor and an anaesthesia vital sign monitor interfaced with a computer to receive input from patient; (b) at least one pump for controlling delivery of drug based on the feedback from patient; (c) said computer having specific software for controlling said pump(s) and for fine tuning the dosage based on patient's response and requirements.

8 Claims, 1 Drawing Sheet

(51) Int. Cl.
*A61M 5/172* (2006.01)
*A61M 16/18* (2006.01)
*G06F 19/00* (2011.01)
*A61M 5/142* (2006.01)
*A61M 16/10* (2006.01)

(52) U.S. Cl.
CPC .. *G06F 19/3468* (2013.01); *A61M 2005/14208* (2013.01); *A61M 2016/1035* (2013.01); *A61M 2205/18* (2013.01); *A61M 2205/50* (2013.01); *A61M 2230/437* (2013.01)

(56) References Cited

U.S. PATENT DOCUMENTS

| | | | |
|---|---|---|---|
| 6,830,047 | B2 | 12/2004 | Heitmeier et al. |
| 6,981,947 | B2 * | 1/2006 | Melker .................... 600/532 |
| 2003/0145854 | A1 * | 8/2003 | Hickle .................... 128/204.18 |
| 2007/0203448 | A1 | 8/2007 | Melker et al. |
| 2007/0282251 | A1 | 12/2007 | Barvais et al. |

* cited by examiner

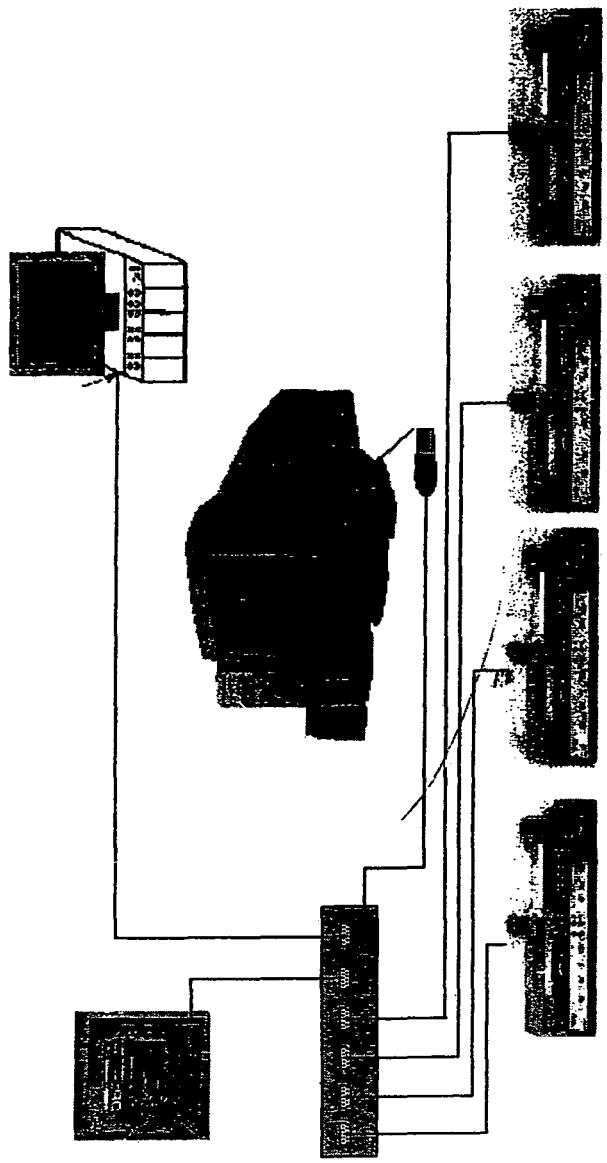

AUTOMATIC ANAESTHESIA DELIVERY SYSTEM

FIELD OF INVENTION

This invention relates to an improved automatic anaesthesia delivery system.

BACKGROUND/PRIOR ART

Anaesthetic agents are administered routinely based on predetermined dose requirement which is according to patients' age and body weight. MAC (Minimum Alveolar concentrations) of anaesthetic agents as well as plasma drug concentrations required for producing anaesthetic state vary in different individuals depending upon the altered drug pharmacokinetic (what body does to the chug) as well as dynamics (what drug does to body) due to different disease states (pathological states) of patient population visiting for anaesthesia and surgery. Even among normal healthy individuals, there are variations in pharmacokinetic (drug disposition by body) and pharmacodynamic (drug effect on body) of anaesthetic drugs used in clinical scenarios. Consequently administration of anaesthetic drugs is titrated using hypertension and tachycardia (alteration in haemodynamics) as indicators of inadequate depth of anaesthesia. However, the disadvantage associated with the same is that, blood pressure and heart rate are not reliable indicators of depth of anaesthesia as a large number of cardiovascular drugs like β-blockers and other anti-hypertensive may affect the blood pressure and heart rate. In view of this, there is need to monitor objectively the drug effect or depth of anaesthesia. EEG has been used to indicate the depth of anaesthesia, but the ideal control variable for the delivery of anaesthetics is still unknown[1]. Various electrophysiological (EEG) variables have been used in an attempt to provide measure of anaesthetic depth[2] though the success is limited[2-4]. Simple measures of EEG like spectral edge frequency (SEF), Median edge frequency (MEF) correlate poorly with clinical parameters of depth of anaesthesia. The Bispectral index (BIS) is a derived variable of the EEG that provides a measure of the consistency of phase and power relationships among the various frequencies of the EEG[5]. The BIS describes the complex EEG pattern as a single variable which has been used for control of anaesthesia and approved by FDA for anesthetic depth monitoring.

Attempts have been made in the West to control anaesthetic agent's delivery using closed loop drug delivery[4,5]. Various parameters such as median frequency of EEG or auditory evoked potentials have been applied as controlled variable for closed loop control of hypnotic anesthetic drugs in the literature.

All these attempts have used Target Controlled infusion pumps for titrating the drug delivery to different indicators of depth of anaesthesia. In spite of that, no closed loop anaesthesia system is available commercially. Target controlled infusion pumps are not only 3-4 times constlier than the simple syringe pump but they also require special prefilled syringes of drug for controlling the delivery of Propofol.

None of the systems developed so far incorporate both intravenous as well as inhalational anaesthetic agents together. None of the system provides versatility to the anaesthetist or user to change from one type of anaesthesia i.e. intravenous anaesthesia to other type of anaesthesia i.e. inhalational anaesthesia and vice versa. None of the system suggested earlier incorporate safety features regarding the effect of anaesthetic agent on blood pressure and heart rate and controlling anaesthetic delivery governed by these factors.

Normally the drug is administered and the monitoring equipment monitors the effect. The clinician reads the display of the monitor and then changes are made in the drug delivery system to alter the rate of delivery of the drug. The process is repeated after observing the changes in the monitored value, which may cause the following:

Time delay in display of the monitored value,
Time delay in reading the value,
Time delay in comprehending the change in monitored value,
Time delay in altering manually the drug delivery,
Human error in reading, judging and altering the drug dosage.

Further, reference may be made to "A new closed-loop control system for isoflurane using Bispectral index wherein Automatic control of depth of hypnosis using the Bispectral-Index (BIS) can help to reduce phases of inadequate control.

Yet further, reference may be made to "Titration of propofol for Anesthetic induction and maintenance guided by the Bispectral index. This report describes a closed-loop titration of propofol target control infusion based on a proportional-differential algorithm guided by the Bispectral Index (BIS) allowing induction and maintenance of general anesthesia and compares this to manual propofol target control infusion.

OBJECTS OF THE INVENTION

The primary object of the present invention is to propose an improved automatic anaesthesia delivery system which overcomes disadvantages of the prior art.

Another object of the present invention is to propose an improved automatic anaesthesia delivery system which controls delivery of anaesthetic agent by closed loop method using BIS as well as inhalational anaesthetic agent concentrations in the lungs.

Still another object of the present invention is to propose an improved automatic anaesthesia delivery system which is efficient.

Further object of the present invention is to propose an improved automatic anaesthesia delivery system which results in reduction of clinical workload and faster response.

STATEMENT OF INVENTION

According to this invention there is provided an improved automatic anaesthesia delivery system comprising of: a) bispectral index monitor and an anaesthesia vital sign monitor interfaced with a computer to receive input from patient; a) at least one syringe infusion pump adapted to change stepwise the rate of delivery of anaesthesia based on feedback from bispectral index monitor as well as vital sign monitor and/or muscle relaxant pump to control the delivery of muscle relaxant drugs based on the feed back from patient through neuromuscular junction monitoring from the vital sign monitor and or analgesic pump to control the rate of injection of analgesic drugs like morphine, Fentanyl ect based on the feed back from vital sign monitor as well as Bispectral index monitor; c) said computer having specific software for controlling the said pump (s) and fine tuning the dosage based on patient's response and requirement.

BRIEF DESCRIPTION OF THE ACCOMPANYING DRAWING

Further objects and advantages of this invention will be more apparent from the ensuing description when read in conjunction with the accompanying drawing and wherein:

FIG. 1 shows: exemplary embodiment of anaesthesia delivery system of the present invention.

DETAILED DESCRIPTION OF THE INVENTION WITH REFERENCE TO THE ACCOMPANYING DRAWING

The present invention constitutes automatic anaesthesia delivery system using closed loop This requires some drug delivery system, which can be controlled using microprocessor based on feed back from the patient. The feedback from patient is anaesthetic depth monitored by BIS as well as end tidal (expired gas) concentrations of the isoflurane (inhalational anaesthetic agent). These are interfaced to a computer which controls the rate of pump according to the requirement.

Reference may be made to FIG. 1. The closed loop control system of the present invention comprises the following components:
1. Control variable (BIS and/or inhalational anaesthetic agent concentration).
2. Set point for the variable, which is target value specified by the user (value of BIS and/or value of end tidal concentration of inhalational anaesthetic agent).
3. Controllers (3) to control the actuator comprising of an algorithm to translate a measured value of the variable to a particular action of the actuator in order to approach the target value and a user interface to set the target value and other settings as required.
4. Safety limits of blood pressure, heart rates as well as carbon dioxide concentrations which can be used to alter the drug delivery rates even stopping them in case of extreme situations.

The actuator comprises anaesthetic infusion pumps (4 and 5), and analgesic and muscle relaxant pump (6 and 7). The anaesthetic infusion pumps are used for the anaesthetic drug administration, which is at least two in number. One infusion pump (4) is used to infuse intravenous anaesthetic drug into patients blood and another one (5) is used to deliver inhalational anaesthetic agent in the patient breathing circuit.

Intravenous anaesthetic agents can be used to induce anaesthesia as well as for maintenance of anaesthesia while inhalational anaesthetic agent are usually/can be used for maintenance of anaesthesia. Intravenous anaesthetic induction is the preferred choice in case of adults or those having intravenous line already in situ because of ease of administration and better acceptability by the patient. Hence, combination of the two modes of anaesthetic delivery in one system has practical advantage and versatility of changing the type of anaesthesia at will. The present system supports the same i.e patient may be induced with intravenous anaesthesia and then maintained on intravenous or inhalational anaesthetic agent as per the need of patient or requirement of clinical situation.

The muscle relaxant pump (6), controls delivery of muscle relaxant drugs [Neuromuscular blocking agent(s)] based on the feedback of neuromuscular junctions monitoring performed through vital sign monitor.

The analgesic pump (7) controls delivery of Morphine or Fetanyl or any other short acting analgesic drug based on the patients' response and requirement judged from the blood pressure, heart rate changes and BIS changes in response to various surgical stimulates.

In this system, the delivery of inhalational anaesthetic drug is based on the feed back of its effect on patient's level of consciousness as well as from its concentration in the expired as well as inspired gases coming from the patient.

Drug delivery system of the present invention is having a set of two syringe infusion pumps out of which one (4) is capable of delivering propofol (an intravenous anaesthetic agent) to the patient and another syringe pump (5) capable of delivering volatile anaesthetic agent at variable rate into the breathing circuit of the patient. Further, it comprises an anaesthesia vital sign monitor (2) (S/5™ anaesthesia monitor, Datex-Ohmeda Inc., Madison, Wis.) including Bispectral Index monitor (1) interfaced with a computer (3). The rate of drug delivery (Propofol or the volatile agent isoflurane) or the rate of syringe pump is altered stepwise based on feedback from BIS module of the vital sign monitor. Target BIS can be set by the user manually around 50 i.e 45-44 as primary control and the concentration of inhalational anaesthetic agent isoflurane in the lungs (determined by end tidal concentration of the isoflurane in the breathing circuit) can also be set by the user as secondary control or vice versa. The algorithm controls the syringe pump rate of propofol (intravenous anaesthetic agent) as well as isoflurane (inhalational anaesthetic agent) and hence rate of drug delivery, propofol or isoflurane depending upon the agent chosen in a particular case. This system is more safe, convenient and economic as compared to manual adjustments of anaesthetic agents for controlling the depth of anaesthesia.

System of the present invention is a unique system to control drug delivery of inhalational anaesthetic drugs using computer in a closed loop system where the inhalational anaesthetic drug delivery is based on the feedback of its effect on the patient's level of consciousness as well as from its concentration in the expired as well as inspired gases coming from the patient. The algorithm and software program for controlling the patients' depth of anaesthesia has been developed based on the clinical pharmacological information of the drugs. This system not only takes care of the requirement of different individuals but also fine-tunes the dosages based on the patient's response and requirement.

In order to make the system compact, the simple syringe pumps, and Bispectral index monitor and muscle relaxant can be incorporated along with anaesthesia vital, sign monitor as a single unit.

The proposed system uses simple syringe pumps rather than target controlled infusion (TCI) pump for the propofol delivery as TCI is costly because of expensive prefilled syringe required for the same. Further, in the present designed system user can shift from intravenous to inhalational anaesthesia or vice versa at his will.

Operation of the System

Infusion Pumps for propofol (intravenous anaesthetic agent) and isoflurane (inhalational anaesthetic agent)

↓

Build up of conc. in the patient's blood by the intravenous anaesthetic agent propofol Or Build up of conc. in the anaesthesia breathing circuit as well as patient's blood by the inhalational agent isoflurane

↓

Drug effect
(BIS monitored)

↓

Feed back to computer

↓

-continued

Alteration in drug delivery based on predetermined set point of BIS alone in case of intravenous agent propofol or BIS and end tidal anaesthetic concentration of isoflurane in case on inhalational anaesthetic agent isoflurane.

Measured BIS, end tidal anaesthetic agent (isoflurane concentration) and drug delivery rate (propofol or isoflurane)

Change in drug delivery rate by altering the rate of respective syringe infusion pumps.

Analgesic and muscle relaxant drug delivery based on the predefined dosages and on top of that, the feedback of blood pressure, heart rate as well as neuromuscular junction monitor from vital sign monitor. All these feedbacks can result in change in rate of drug delivery of both analgesic (morphine, fentanyl ect) as well as Muscle relaxant (Vecuronium, Pancuronium etc).

Utility Aspects:

This system allows automatic delivery of anaesthetic agent to the patient at the time of induction of anaesthesia using intravenous or inhalational (gaseous anaesthetic agents) anaesthetic agents depending upon the patient's condition or choice of anaesthetist.

If frees the anaesthetist from the repetitive task of looking at the anaesthetic depth and altering the drug delivery manually.

It frees anaesthetist's hands to allow him/her to do other activities while keeping a watch on the monitor.

Anaesthetist is warned of the abnormal rates of drug delivery as well as abnormal response of the patient through visual and audio warning.

It allows fine-tuning of the drug delivery according to the requirement of the patient as well as the surgical stimulus requirement.

It allows safety of patient by cutting off anaesthetic drug delivery in case of severe drop in blood pressure or heart rate.

It allows the anaesthetist to define the safety limits of blood pressure as well as heart rate and blood gas levels for not only warning the anaesthetist but also stopping delivery of the anaesthetic agents.

It also allows the anaesthetist to define the inspired and expired concentrations of anaesthetic agent beyond which the system stops delivery of anaesthetic agent.

This system can be incorporated in the syringe pump itself during the production phase to make it more compact and practical.

Potent drugs may have onset of action in the range of 15 seconds. Similarly the offset of action is measurable in seconds in large number of potent drugs, which are controlled with syringe infusion pumps. Use of microprocessor helps in achieving fast rate of monitoring and adjusting rate of drug administration. The clinician will be able to devote his/her time to other intervention like venous line maintenance, endrotracheal intubation, bronchoscopy, defibrillation, other resuscitative measures etc.

Advantageous Features of the Present Invention

Closed loop or feedback controlled drug delivery system offers considerable benefits in clinical practice. Among the advantages cited is
1. Reduced clinical workload.
2. Reduction of the amount of drug required to achieve a particular effect.
3. Greater stability of the measured variable under closed loop control system.
4. Faster response.

Closed loop feedback controlled administration of drugs offers considerable benefits in clinical practice. These automated drug delivery systems manage some output (control variable such as blood pressure or neuromuscular blockade) based on information obtained from an input signal. The stability of the monitored variable under automatic control is usually better than that can be achieved by manual means by virtue of more frequent sampling of the measured variable and control adjustments. However, the clinician always has the opportunity of overriding the automatic control system.

It is to be noted that the present invention is susceptible to modifications, adaptations and changes by those skilled in the art. Such variant embodiments employing the concepts and features of this invention are intended to be within the scope of the present invention, which is further set forth under the following claims:

I claim:
1. An improved automatic anaesthesia delivery system comprising:
(a) a bispectral index monitor and an anaesthesia vital sign monitor interfaced with a computer to receive feedback from a patient;
(b) a first pump for controlling delivery of an inhalation anaesthetic drug; and
(c) a second pump for controlling delivery of an intravenous anaesthetic drug,
wherein said computer comprises software for controlling said first pump and said second pump based on the feedback from said patient, and
wherein the system can be changed from delivering the inhalation anaesthetic drug to the intravenous anaesthetic drug or vice-versa during use of the system.

2. The improved automatic anaesthesia delivery system as claimed in claim 1, wherein the first pump or the second pump is a syringe pump.

3. The improved automatic anaesthesia delivery system as claimed in claim 2, further comprising a muscle relaxant pump for controlling delivery of drugs based on the feedback from the patient, wherein the anaesthesia vital sign monitor monitors a neuromuscular junction, wherein the feedback comprises blood pressure, heart rate changes, and BIS changes, and wherein the drug is a muscle relaxant, morphine, Fentanyl, or any other short acting analgesic.

4. The improved automatic anaesthesia delivery system as claimed in claim 1, wherein the bispectral index monitor can be made a primary control and the anaesthesia vital sign monitor can be made a secondary control.

5. The improved automatic anaesthesia delivery system as claimed in claim 1, wherein the anesthesia vital sign monitor can be made a primary control and the bispectral index monitor can be made a secondary control.

6. The improved automatic anaesthesia delivery system as claimed in claim 1 wherein the software stops the delivery of either the inhalation anaesthetic drug or the intravenous anaesthetic drug when the patient has a severe drop in blood pressure or heart rate.

7. The improved anaesthesia delivery system as claimed in claim 1 wherein the software comprises safety limits that can be set by an operator for blood pressure, heart rate and blood gas levels to provide a warning or to stop delivery of either the inhalation anaesthetic drug or the intravenous anaesthetic drug.

8. The improved anaesthesia delivery system as claimed in claim 1 wherein the system provides a warning for an abnormal rate of delivery of either the inhalation anaesthetic drug or the intravenous anaesthetic drug; or an abnormal response by the patient.

* * * * *

UNITED STATES PATENT AND TRADEMARK OFFICE
CERTIFICATE OF CORRECTION

PATENT NO. : 9,108,013 B2  
APPLICATION NO. : 12/683000  
DATED : August 18, 2015  
INVENTOR(S) : Goverdhan Dutt Puri Page 1 of 1

It is certified that error appears in the above-identified patent and that said Letters Patent is hereby corrected as shown below:

Title Page, Item (73) Assignees, Line 4, delete "Chanlgarh" and insert -- Chandigarh --

Signed and Sealed this
Nineteenth Day of July, 2016

Michelle K. Lee
*Director of the United States Patent and Trademark Office*